(12) United States Patent
Sato et al.

(10) Patent No.: US 9,881,796 B2
(45) Date of Patent: Jan. 30, 2018

(54) METHOD FOR MANUFACTURING MOLYBDENUM OXIDE-CONTAINING THIN FILM

(71) Applicant: ADEKA CORPORATION, Tokyo (JP)

(72) Inventors: Hiroki Sato, Tokyo (JP); Junji Ueyama, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/823,293

(22) Filed: Aug. 11, 2015

(65) Prior Publication Data

US 2015/0371859 A1 Dec. 24, 2015

Related U.S. Application Data

(62) Division of application No. 14/112,125, filed as application No. PCT/JP2012/062199 on May 11, 2012, now abandoned.

(30) Foreign Application Priority Data

May 27, 2011 (JP) .................................. 2011-118760

(51) Int. Cl.
*H01L 21/28* (2006.01)
*C23C 16/40* (2006.01)
(Continued)

(52) U.S. Cl.
CPC ...... *H01L 21/28194* (2013.01); *C07F 11/005* (2013.01); *C23C 16/40* (2013.01);
(Continued)

(58) Field of Classification Search
None
See application file for complete search history.

(56) References Cited

U.S. PATENT DOCUMENTS 6,114,242 A 9/2000 Sun et al.
6,238,734 B1 5/2001 Senzaki et al.
(Continued)

FOREIGN PATENT DOCUMENTS

FR 2883287 * 9/2006
JP 2001-081560 3/2001
(Continued)

OTHER PUBLICATIONS

Vautier FR2883287 English machine translation. Sep. 2006.*
(Continued)

*Primary Examiner* — Joseph A Miller, Jr.
(74) *Attorney, Agent, or Firm* — Young & Thompson

(57) ABSTRACT

Disclosed is a method for manufacturing a molybdenum oxide-containing thin film, involving vaporizing a starting material for forming a thin film containing a compound represented by the following general formula (I) to give vapor containing a molybdenum amide compound, introducing the obtained vapor onto a substrate, and further introducing an oxidizing gas to cause decomposition and/or a chemical reaction to form a thin film on the substrate. In the formula, $R^1$ and $R^2$ each represents a straight or branched alkyl group having 1 to 4 carbon atom(s), $R^3$ represents a t-butyl group or a t-amyl group, y represents 0 or 2, x is 4 when y is 0, or x is 2 when y is 2, wherein $R^1$ and $R^2$ that are plurally present may be the same or different.

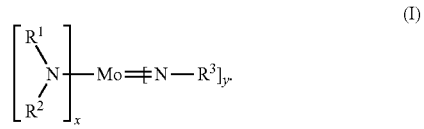

(I)

6 Claims, 3 Drawing Sheets

(51) Int. Cl.
- *C07F 11/00* (2006.01)
- *C23C 16/455* (2006.01)
- *H01L 29/51* (2006.01)
- *H01L 21/285* (2006.01)
- *H01L 21/768* (2006.01)
- *H01L 29/49* (2006.01)

(52) U.S. Cl.
CPC ...... *C23C 16/405* (2013.01); *C23C 16/45553* (2013.01); *H01L 21/28556* (2013.01); *H01L 21/76841* (2013.01); *H01L 29/4966* (2013.01); *H01L 29/517* (2013.01); *Y02E 10/541* (2013.01); *Y02P 70/521* (2015.11)

(56) References Cited

U.S. PATENT DOCUMENTS

| | | | |
|---|---|---|---|
| 6,359,160 | B1 | 3/2002 | Sun et al. |
| 6,416,890 | B1 | 7/2002 | Terneu et al. |
| 6,552,209 | B1 | 4/2003 | Lei et al. |
| 7,560,581 | B2 | 7/2009 | Gordon et al. |
| 7,956,207 | B2 | 6/2011 | Meiere et al. |
| 2001/0050028 | A1* | 12/2001 | Itsuki ............... C07F 7/006 106/1.22 |
| 2004/0198069 | A1* | 10/2004 | Metzner ............. C23C 16/308 438/785 |
| 2006/0125099 | A1 | 6/2006 | Gordon et al. |
| 2006/0151852 | A1 | 7/2006 | Senzaki |
| 2008/0081922 | A1 | 4/2008 | Meiere et al. |
| 2008/0128772 | A1 | 6/2008 | Senzaki |
| 2009/0026554 | A1* | 1/2009 | Winstead .......... H01L 29/7848 257/408 |
| 2013/0143383 | A1* | 6/2013 | Malhotra .......... H01L 21/32051 438/396 |

FOREIGN PATENT DOCUMENTS

| | | |
|---|---|---|
| JP | 2003-342732 | 12/2003 |
| JP | 2005-533178 | 11/2005 |
| JP | 2005-534180 | 11/2005 |
| JP | 2010-505002 | 2/2010 |

OTHER PUBLICATIONS

Chiu_et_al-2000-Chemical_Vapor_Deposition vol. 6 p. 223.*
International Search Report, PCT/JP2012/062199, dated Jul. 31, 2012.
Ville Miikkulainen, et al., Bis (tert-butylimido)-bis (dialkylamido) Complexes of Molybdenum as Atomic Layer Deposition (ALD) Precursors for Molybdenum Nitride: the Effect of the Alkyl Group, Chemical Vapor Deposition, 2008, vol. 14, p. 71-77.
Dezelah, C., et al. "A Pyrazolate-Based Metalorganic Tantalum Precursor That Exhibits High Thermal Stability and Its Use in the Atomic Layer Deposition of Ta2O5" American Chemical Society, vol. 129, No. 41, 2007, pp. 12370-12371, publication date: Sep. 26, 2007.
Vautier, FR2883287, english machine translation, Sep. 2006.
Miikkulainen Surface and Coatings Tech V202 2008 p. 51 03-5109.

* cited by examiner

METHOD FOR MANUFACTURING MOLYBDENUM OXIDE-CONTAINING THIN FILM

TECHNICAL FIELD

The present invention relates to a method for manufacturing a molybdenum oxide-containing thin film using vapor formed by vaporizing a molybdenum amide compound having a specific ligand, a molybdenum oxide-containing thin film manufactured by the manufacture method, a starting material for forming a molybdenum oxide-containing thin film used for the manufacture method, and a novel molybdenum amide compound having a t-amylimide group as a ligand.

BACKGROUND ART

Molybdenum oxide-containing thin films can be used for organic light-emitting diodes, liquid crystal displays, plasma display panels, field emission displays, thin film solar batteries, low resistance ohmics, and other electronic devices and semiconductor devices, and are mainly used as elements for electronic parts such as barrier films.

Examples of a method for manufacturing the above-mentioned thin film may include a flame deposition process, a sputtering process, an ion plating process, MOD processes such as a coating-pyrolysis process and a sol-gel process, a chemical vapor deposition process, and the like, and a chemical vapor deposition (hereinafter sometimes simply referred to as CVD) process including an ALD (Atomic Layer Deposition) process is an appropriate manufacture process, because of the many advantages of the process including excellent properties in composition control and step coverage, suitability for mass manufacture, capability of providing hybrid integration, and the like.

As starting materials for the chemical vapor phase deposition process for the manufacture of a molybdenum oxide-containing thin film, organic molybdenum compounds such as molybdenum carbonyl [$Mo(CO)_6$], molybdenum acetylacetonate, molybdenum chloride ($MoCl_3$ or $MoCl_5$), molybdenum fluoride ($MoF_6$) and $MoO_2$ (2,2,6,6-tetramethylheptane-3,5-dione)$_2$, and molybdenum oxychloride ($MoO_2Cl_2$ or $MoOCl_4$) are reported in Patent Literature 1. Furthermore, a molybdenum amide imide compound is reported as a starting material for the formation of a molybdenum nitride thin film by ALD in Non-patent Literature 1.

In a method for manufacturing a molybdenum oxide-containing thin film including introducing vapor obtained by vaporizing a starting material for forming a thin film into a substrate, and further decomposing and/or chemically reacting the vapor by introducing oxidizing gas to form a thin film on the substrate, there is no report about the method for manufacturing a thin film using a molybdenum amide compound according to the present invention.

CITATION LIST

Patent Literature

Patent Literature 1: U.S. Pat. No. 6,416,890

Non-Patent Literature

Non-patent Literature 1: Chem. Vap. Deposition 2008, 14, 71-77

SUMMARY OF INVENTION

Technical Problem

In the manufacture of a molybdenum oxide-containing thin film by a CVD process, it was not necessarily able to be considered that the molybdenum compounds that had been suggested in the past had sufficient properties. The properties required for a compound (precursor) that is suitable for a starting material for forming a thin film by vaporizing a compound in a CVD process and the like are that the compound has a low melting point; the compound has a temperature difference between the melting point and boiling point such that a liquid state can be stably retained during the manufacture of a molybdenum oxide-containing thin film, and thus the compound can be stably transported in a liquid state; and the compound has a high vapor pressure and thus is easily vaporized. The compounds that had been used as conventional molybdenum sources were solids or had a small temperature difference between the melting point and boiling point, and thus had problems of poor precursor transportation property and a low vapor pressure in a CVD process. Furthermore, when a molybdenum compound containing a fluorine atom was used as a molybdenum source for the manufacture of a molybdenum oxide-containing thin film by a CVD process, there was a problem that hydrogen fluoride sometimes generated as a reaction by-product during the manufacture of the thin film and caused a device to corrode.

Solution to Problem

The present inventors did various studies, and consequently found that a method for manufacturing a molybdenum oxide-containing thin film by a CVD process using a specific molybdenum amide compound as a precursor can resolve the above-mentioned problems, and attained the present invention.

The present invention provides a method for manufacturing a molybdenum oxide-containing thin film, comprising, vaporizing a starting material for forming a thin film containing a compound represented by the following general formula (I) to give vapor containing a molybdenum amide compound, introducing the obtained vapor onto a substrate, and further introducing an oxidizing gas to cause decomposition and/or a chemical reaction to form a thin film on the substrate.

[Chemical Formula 1]

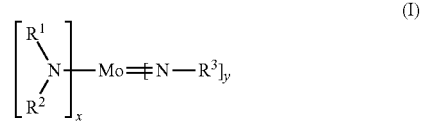

(I)

wherein $R^1$ and $R^2$ each represents a straight or branched alkyl group having 1 to 4 carbon atom(s), $R^3$ represents a t-butyl group or a t-amyl group, y represents 0 or 2, and x is 4 when y is 0, or x is 2 when y is 2, wherein $R^1$ and $R^2$ that are plurally present may be the same or different.

Furthermore, the present invention provides a starting material for forming a molybdenum oxide-containing thin film, containing the compound represented by the above-mentioned general formula (I) used for the above-mentioned method for manufacturing a thin film.

Furthermore, the present invention provides a novel compound represented by the following general formula (II).

[Chemical Formula 2]

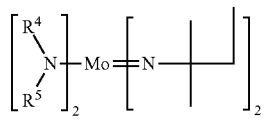

(II)

wherein $R^4$ and $R^5$ each represents a straight or branched alkyl group having 1 to 4 carbon atom(s).

Advantageous Effects of Invention

According to the present invention, since the molybdenum amide compound according to the present invention is a low melting point compound that becomes a liquid at an ordinary temperature or by slight warming, has a significant temperature difference between the melting point and boiling point, and has a high vapor pressure, the precursor-transport property is excellent, and the supply amount to the substrate is easily controlled and stable supplying is possible in the manufacture of a molybdenum oxide-containing thin film by a CVD process, and thus a molybdenum oxide-containing thin film having a fine quantity manufacture property and a fine quality can be manufactured.

DESCRIPTION OF EMBODIMENTS

Figure 1:
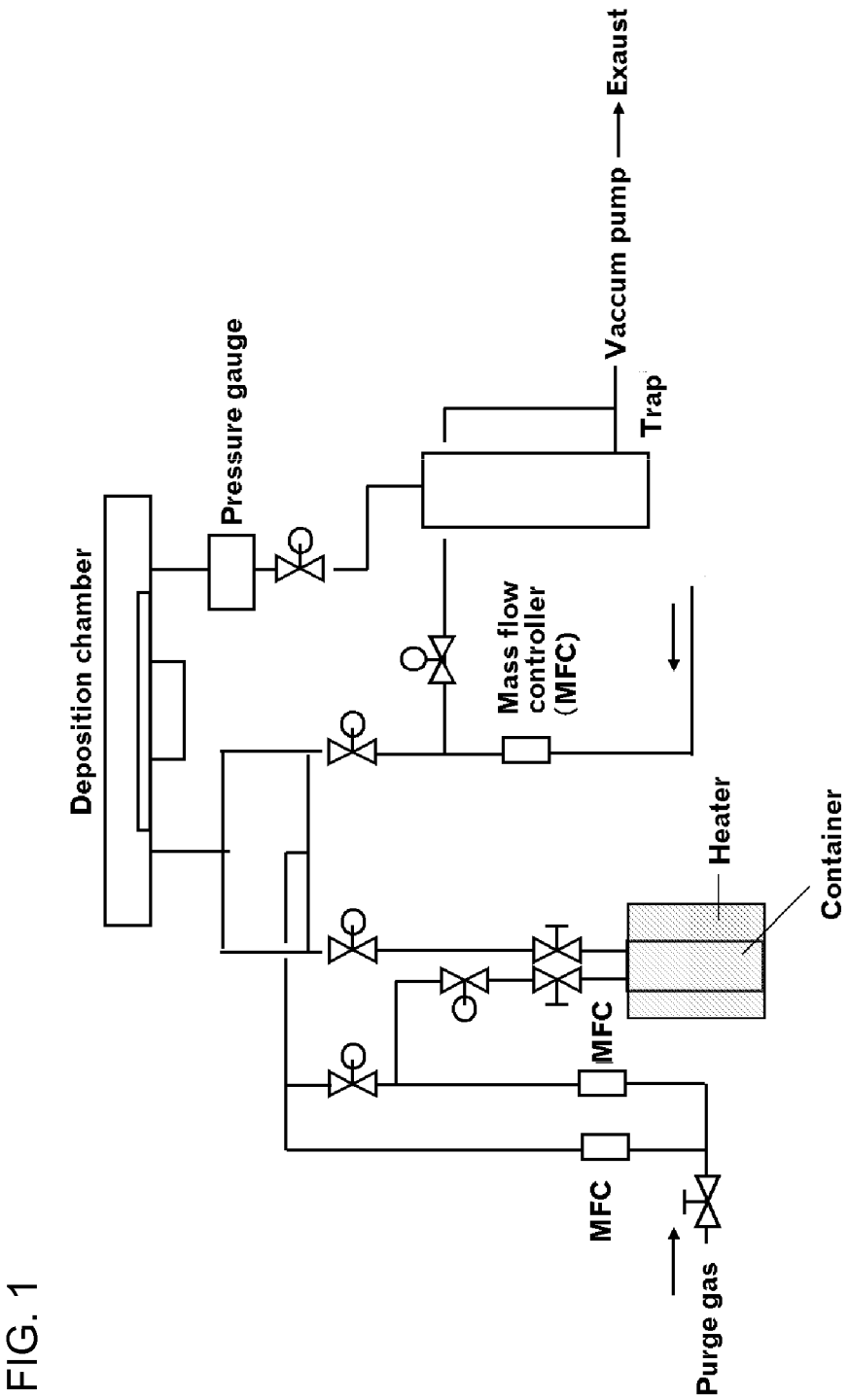
FIG. 1 is a schematic drawing showing an example of an apparatus for chemical vapor deposition, which is used for the method for manufacturing a molybdenum oxide-containing thin film of the present invention.

Hereinafter the method for manufacturing a molybdenum oxide-containing thin film of the present invention will be explained in detail with referring to preferable exemplary embodiments thereof.

In the above-mentioned general formula (I) representing the molybdenum amide compound of the present invention, examples of the straight or branched alkyl group having 1 to 4 carbon atom(s) represented by $R^1$ and $R^2$ may include methyl, ethyl, propyl, isopropyl, butyl, s-butyl, t-butyl and isobutyl, examples of $R^3$ may include t-butyl or t-amyl, y represents 0 or 2, x is 4 when y is 0, or x is 2 when y is 2, wherein $R^1$ and $R^2$ that are plurally present may be the same or different. Specific examples of the molybdenum amide compound, which is a ligand compound having such groups, may include compounds No. 1 to 81 shown below. However, the present invention is not construed to be limited at all by the following exemplary compounds.

[Chemical Formula 3]

Compound No. 1

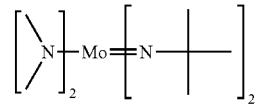

Compound No. 2

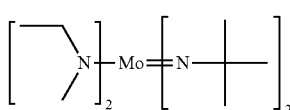

Compound No. 3

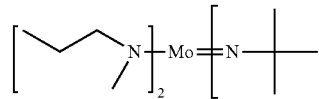

Compound No. 4

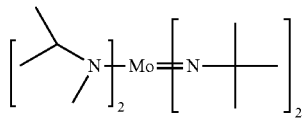

Compound No. 5

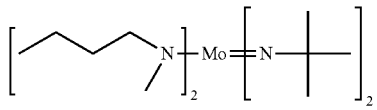

Compound No. 6

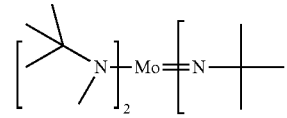

Compound No. 7

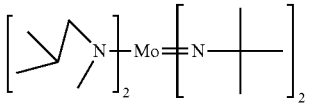

Compound No. 8

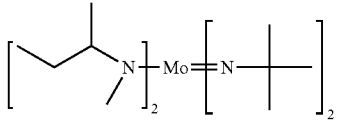

[Chemical Formula 4]

Compound No. 9

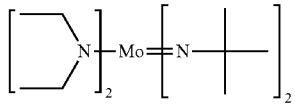

Compound No. 10

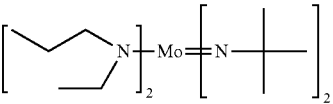

Compound No. 11

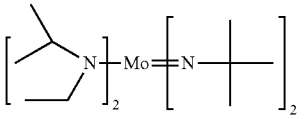

-continued
Compound No. 12
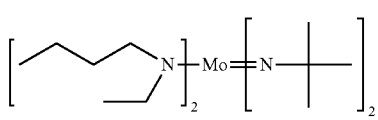
Compound No. 13
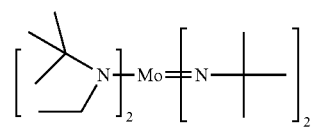
Compound No. 14
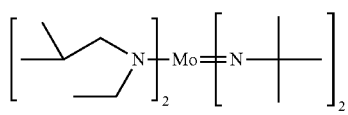
Compound No. 15
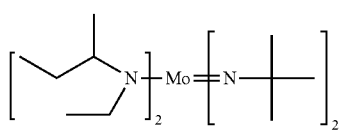
[Chemical Formula 5]
Compound No. 16
Compound No. 17
Compound No. 18
Compound No. 19
Compound No. 20
Compound No. 21
Compound No. 22
Compound No. 23
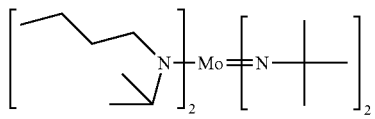
Compound No. 24
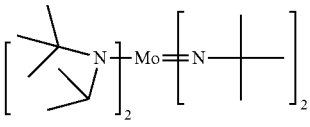
Compound No. 25
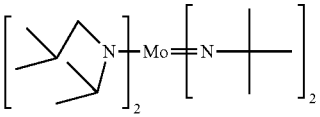
Compound No. 26
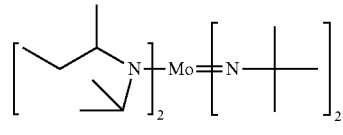
[Chemical Formula 6]
Compound No. 27
Compound No. 28
Compound No. 29
Compound No. 30
Compound No. 31
Compound No. 32
Compound No. 33

-continued
Compound No. 34
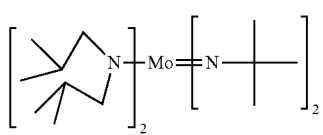
Compound No. 35
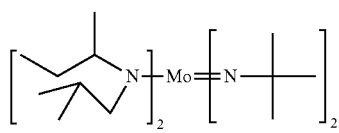
Compound No. 36
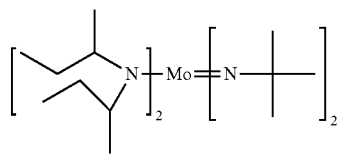
[Chemical Formula 7]
Compound No. 37
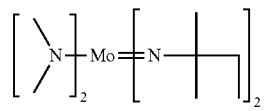
Compound No. 38
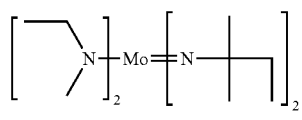
Compound No. 39
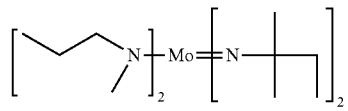
Compound No. 40
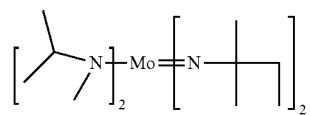
Compound No. 41
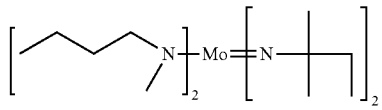
Compound No. 42
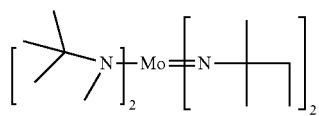
Compound No. 43
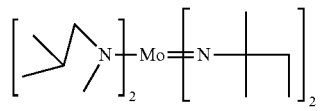
Compound No. 44
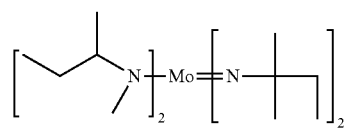
-continued
[Chemical Formula 8]
Compound No. 45
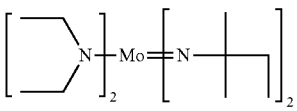
Compound No. 46
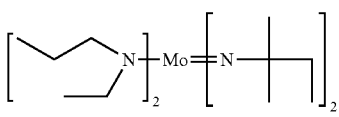
Compound No. 47
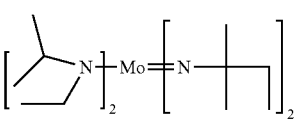
Compound No. 48
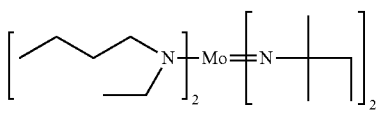
Compound No. 49
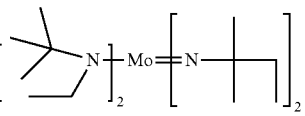
Compound No. 50
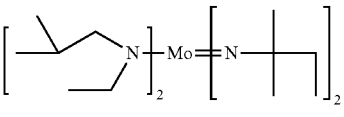
Compound No. 51
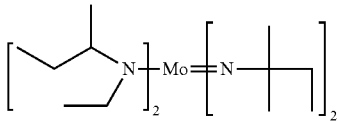
[Chemical Formula 9]
Compound No. 52
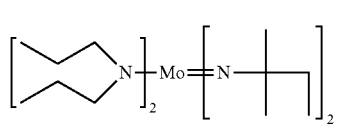
Compound No. 53
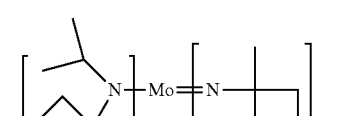
Compound No. 54
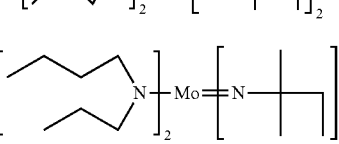
Compound No. 55
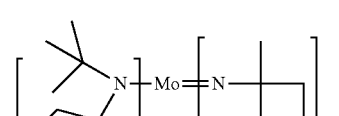
Compound No. 56
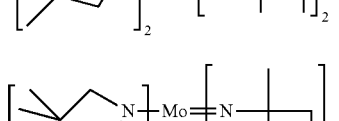

-continued
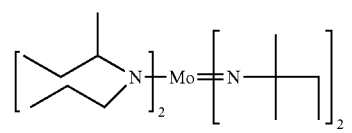
Compound No. 57
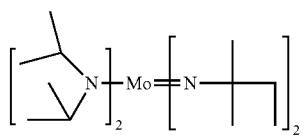
Compound No. 58
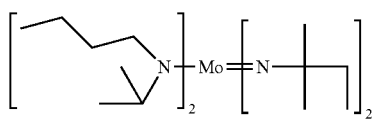
Compound No. 59
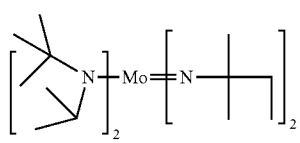
Compound No. 60
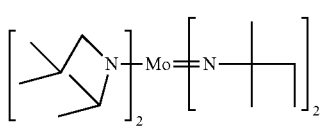
Compound No. 61
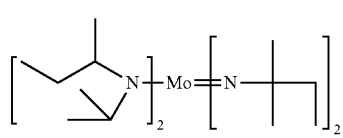
Compound No. 62
[Chemical Formula 10]
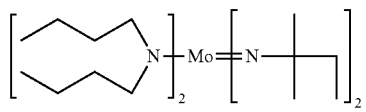
Compound No. 63
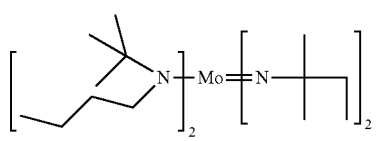
Compound No. 64
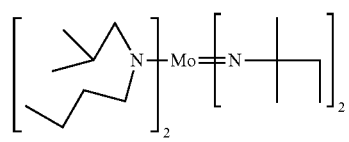
Compound No. 65
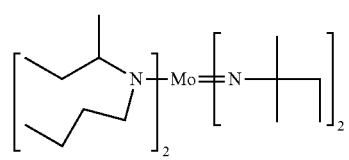
Compound No. 66
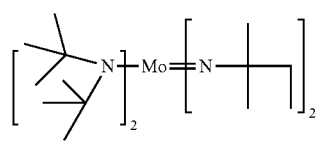
Compound No. 67
-continued
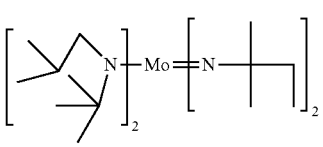
Compound No. 68
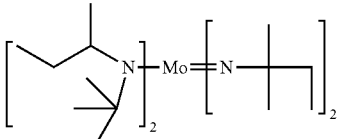
Compound No. 69
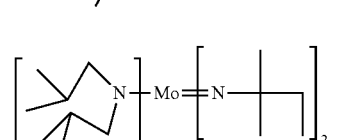
Compound No. 70
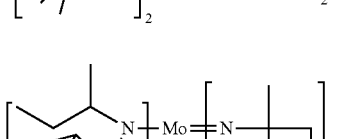
Compound No. 71
Compound No. 72
[Chemical Formula 11]
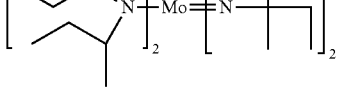
Compound No. 73
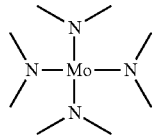
Compound No. 74
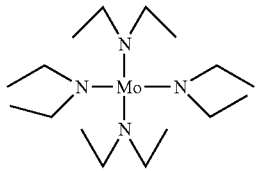
Compound No. 75
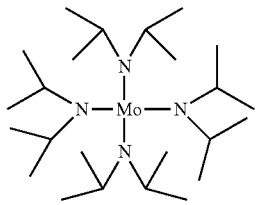
Compound No. 76
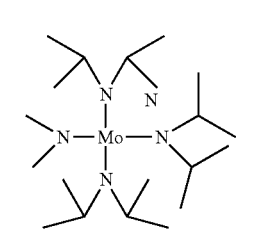

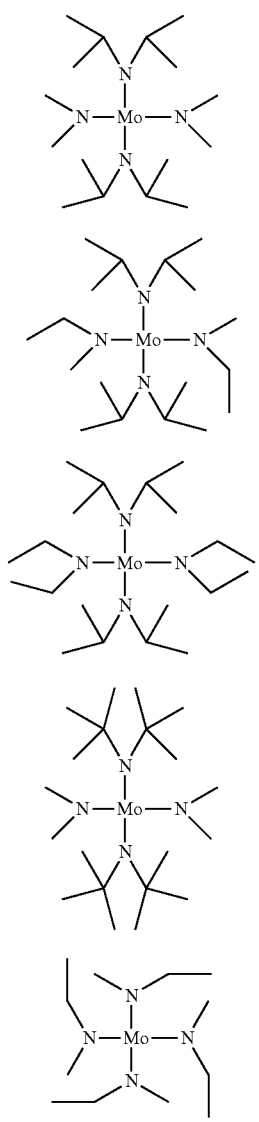

Compound No. 77

Compound No. 78

Compound No. 79

Compound No. 80

Compound No. 81

In the molybdenum amide compound used for the method for manufacturing a molybdenum oxide-containing thin film of the present invention, $R^1$ to $R^3$ in the above-mentioned general formula (I) are preferably groups such that the compound is a liquid and has a high vapor pressure, and specifically, when x and y are 2, $R^1$ and $R^2$ are each preferably a methyl group or an ethyl group, and $R^3$ is a t-butyl group or a t-amyl group. Compounds wherein $R^3$ is a t-butyl group are specifically preferable since they give a high vapor pressure. When x is 4 and y is 0, $R^1$ and $R^2$ are each preferably a methyl group or an ethyl group.

The starting material for forming a thin film of the present invention contains the molybdenum amide compound explained above as a precursor for the manufacture of a molybdenum oxide-containing thin film, and differs in form depending on the process. The molybdenum amide compound according to the present invention is specifically useful as a starting material for a chemical vapor deposition process for its physical properties.

In the case when the starting material for forming a thin film of the present invention is a starting material for a chemical vapor deposition process, the form thereof is suitably selected depending on techniques such as transport and supply method used in the chemical vapor deposition process.

As the above-mentioned transport and supply method, there are a gas carrier process involving vaporizing a starting material for chemical vapor deposition by heating and/or reducing pressure in a starting material container, and introducing the resulting vapor, if necessary, together with carrier gas such as argon, nitrogen and helium, into a deposition reaction unit; and a liquid carrier process involving transporting a starting material for chemical vapor deposition in a liquid or solution state to a vaporization chamber, vaporizing the starting material by heating and/or reducing pressure in the vaporization chamber, and introducing the obtained vapor into a deposition reaction unit. In the case of the gas carrier process, the molybdenum amide compound itself represented by the above-mentioned general formula (I) is a starting material for chemical vapor deposition, and in the case of the liquid carrier process, the molybdenum amide compound itself represented by the above-mentioned general formula (I) or a solution in which the compound is dissolved in an organic solvent is a starting material for chemical vapor deposition.

In a chemical vapor deposition process of a multi-component system, there are a method involving vaporizing and supplying independently each component of starting materials for chemical vapor deposition (hereinafter also referred to as a single source process) and a method involving vaporizing and supplying a mixed starting material that is prepared by mixing multi-component starting materials at a desired composition in advance (hereinafter also referred to as a cocktail source process). In the case of the cocktail source process, a mixture or mixed solution of the molybdenum amide compound according to the present invention and the other precursor is the starting material for chemical vapor deposition.

The organic solvent used for the above-mentioned starting material for chemical vapor deposition is not specifically limited, and general organic solvents that are well-known can be used. Examples of the organic solvents may include acetate esters such as ethyl acetate, butyl acetate and methoxyethyl acetate; ether alcohols such as ethylene glycol monomethyl ether, ethylene glycol monoethyl ether, ethylene glycol monobutyl ether and diethylene glycol monoethyl ether; ethers such as tetrahydrofuran, tetrahydropyran, ethylene glycol dimethyl ether, diethylene glycol dimethyl ether, triethylene glycol dimethyl ether, dibutyl ether and dioxane; ketones such as methyl butyl ketone, methyl isobutyl ketone, ethyl butyl ketone, dipropyl ketone, diisobutyl ketone, methyl amyl ketone, cyclohexanone and methylcyclohexanone; hydrocarbons such as hexane, cyclohexane, methylcyclohexane, dimethylcyclohexane, ethylcyclohexane, heptane, octane, toluene and xylene; hydrocarbons having a cyano group such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane and 1,4-dicyanobenzene; pyridine and lutidine, and these are used alone or as a mixed solvent of two or more depending on the solubility of the solute, the relationship of the use temperature, boiling point and ignition point, and the like. In the case when these organic solvents are used, these are preferably used in such a manner that the total amount of the molybdenum amide compound according to the present invention and the other precursor in the organic solvent becomes 0.01 to 2.0 mol/liter, specifically 0.05 to 1.0 mol/liter.

Furthermore, the other precursor that is used together with the molybdenum amide compound according to the present invention in the case of the starting material for chemical vapor deposition of a multi-component system is not specifically limited, and general well-known precursors that are used in starting materials for chemical vapor deposition can be used.

Examples of the above-mentioned other precursors may include compounds of one or two or more of organic coordinated compound(s) such as alcohol compounds, glycol compounds, β-diketone compounds, cyclopentadiene compounds and organic amine compounds with silicon or metals. Examples of the metal species for the precursors may include lithium, sodium, potassium, magnesium, calcium, strontium, barium, titanium, zirconium, hafnium, vanadium, niobium, tantalum, molybdenum, manganese, iron, ruthenium, cobalt, rhodium, iridium, nickel, palladium, platinum, copper, silver, gold, zinc, aluminum, gallium, indium, germanium, tin, lead, antimony, bismuth, yttrium, lantern, cerium, praseodymium, neodymium, promethium, samarium, europium, gadolinium, terbium, dysprosium, holmium, erbium, thulium and ytterbium.

Examples of the alcohol compounds used as the above-mentioned organic ligands may include alkyl alcohols such as methanol, ethanol, propanol, isopropanol, butanol, 2-butanol, isobutanol, t-butanol, amyl alcohol, isoamyl alcohol and t-amyl alcohol; ether alcohols such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-s-butoxy-1,1-diethylethanol and 3-methoxy-1,1-dimethylpropanol.

Examples of the glycol compounds used as the above-mentioned organic ligands may include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol and 2,4-dimethyl-2,4-pentanediol.

Examples of the β-diketone compounds used as the above-mentioned organic ligands may include alkyl-substituted β-diketones such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione 2-methyl-6-ethyldecane-3,5-dione and 2,2-dimethyl-6-ethyldecane-3,5-dione; fluorine-substituted alkyl β-diketones such as 1,1,1-trifluoropentane-2,4-dione, 1,1,1-trifluoro-5,5-dimethylhexane-2,4-dione, 1,1,1,5,5,5-hexafluoropentane-2,4-dione and 1,3-diperfluorohexylpropane-1,3-dione; ether-substituted β-diketones such as 1,1,5,5-tetramethyl-1-methoxyhexane-2,4-dione, 2,2,6,6-tetramethyl-1-methoxyheptane-3,5-dione and 2,2,6,6-tetramethyl-1-(2-methoxyethoxy)heptane-3,5-dione.

Examples of the cyclopentadiene compounds used as the above-mentioned organic ligands may include cyclopentadiene, methylcyclopentadiene, ethylcyclopentadiene, propylcyclopentadiene, isopropylcyclopentadiene, butylcyclopentadiene, s-butylcyclopentadiene, isobutylcyclopentadiene, t-butylcyclopentadiene, dimethylcyclopentadiene, tetramethylcyclopentadiene and the like; and examples of the organic amine compounds used as the organic ligands may include methylamine, ethylamine, propylamine, isopropylamine, butylamine, s-butylamine, t-butylamine, isobutylamine, dimethylamine, diethylamine, dipropylamine, diisopropylamine, ethylmethyl amine, propylmethylamine, isopropylmethylamine and the like.

As the above-mentioned other precursors, a compound having similar thermal and/or chemical decomposition behaviors is preferable for the single source process, and a compound causing no chemical alteration during mixing in addition to having similar thermal and/or chemical decomposition behaviors is preferable for the cocktail source process.

The starting material for the chemical vapor deposition of the present invention is designed to reduce the components of impurity metal elements, impurity halogen such as impurity chlorine, and organic impurities, except for components constituting the material to a minimum. The amount of the impurity metal elements is preferably 100 ppb or less per element and more preferably 10 ppb or less, and the total amount of the impurity metal elements is preferably 1 ppm or less and more preferably 100 ppb or less. For use as a gate insulating film, a gate film or a barrier film of LSIs, the amounts of alkali metal elements, alkaline earth metal elements and family elements (chromium or tungsten), which have an effect on the electrical properties of the resulting thin film, are required to be minimized. The amount of the impurity halogen is preferably 100 ppm or less, more preferably 10 ppm or less, and still more preferably 1 ppm or less. The total amount of the organic impurities is preferably 500 ppm or less, more preferably 50 ppm or less, and still more preferably 10 ppm or less. Furthermore, since moisture causes generation of particles in the starting material for the chemical vapor deposition or generation of particles in the course of the formation of the thin film, moisture is desirably removed from the metal compounds, organic solvents, and nucleophilic reagents to reduce the moisture content of each material as much as possible before use. The moisture content in each of the metal compounds, organic solvents, and nucleophilic reagents is preferably 10 ppm or less, and more preferably 1 ppm or less.

Further, in order to reduce or prevent particle contamination in a thin film manufactured, it is preferable to decrease particles to a minimum in the starting material for the chemical vapor deposition of the present invention. Specifically, as measured with a light scattering type liquid-borne particle sensor in a liquid phase, it is preferable that the number of particles having a diameter of 0.3 μm or larger is 100 or less per 1 ml of the liquid phase, it is more preferable that the number of particles having a diameter of 0.2 μm or larger is 1,000 or less per 1 ml of the liquid phase, and it is even more preferable that the number of particles having a diameter of 0.2 μm or larger is 100 or less per 1 ml of the liquid phase.

The method for manufacturing a molybdenum oxide-containing thin film according to the present invention is a chemical vapor deposition process involving introducing a gas containing a molybdenum amide compound formed by vaporizing the compound represented by the above-mentioned formula (I), and a gas obtained by vaporizing other precursor used as necessary and an oxidative gas onto a substrate, and decomposing and/or chemically reacting the molybdenum amide compound and the other precursor used as necessary on the substrate to form a thin film on the substrate. There are no particular limitations on transport and supply methods of the starting material, deposition methods, manufacture conditions, manufacture apparatus and the like, and generally well-known methods and conditions can be used.

Examples of the oxidizing gas used in the method for manufacturing a molybdenum oxide-containing thin film according to the present invention may include oxygen, singlet oxygen, ozone, carbon dioxide, nitrogen monoxide, nitrogen dioxide, water, hydrogen peroxide, formic acid, acetic acid, acetic anhydride and the like, and one or two or more of these can be used. The above-mentioned oxidizing gas containing ozone, oxygen or water is preferably used since the residual carbon in the film can further be decreased.

Examples of the above-mentioned transport and supply methods may include the gas carrier methods, liquid carrier methods, single source processes, cocktail source processes described above, and the like.

The above-mentioned deposition methods include a thermal CVD process in which the molybdenum amide compound (and the other precursor gas) and reactive gas are reacted only by heat in order to deposit a thin film, a plasma CVD process in which heat and plasma are used, a photo CVD process in which heat and light are used, a photo-plasma CVD process in which heat, light and plasma are used, and an ALD process in which a deposition reaction in a CVD process is separated into elementary steps and deposition is carried out step by step in a molecular level.

The above-mentioned manufacture conditions include a reaction temperature (substrate temperature), a reaction pressure, a deposition rate and the like. The reaction temperature is preferably 100° C. or more at which the molybdenum amide compound according to the present invention is sufficiently reacted, and is more preferably 100° C. to 300° C. The reaction pressure is preferably 0.01 Pa to 300 Pa for the thermal CVD process, photo CVD process and plasma CVD process. The deposition rate may be controlled by the supply conditions (vaporization temperature and vaporization pressure) of the starting material and the reaction temperature and pressure. When the deposition rate is high, the resulting thin film possibly has poor properties, whereas when the deposition rate is low, there may be a problem with the productivity; thus, the deposition rate is preferably 0.2 to 40.0 nm/min and more preferably 4.0 to 25.0 nm/min. In the case of the ALD process, a desired thickness is obtained by controlling the number of cycles.

For example, in the case when a molybdenum oxide thin film is formed by the ALD process, a precursor thin film is formed on the substrate by the molybdenum amide compound that has been introduced in the deposition reaction unit, after the step of introducing the starting material explained above (a step of forming a precursor thin film). At this time, heat may be applied by heating the substrate or heating the deposition reaction unit. The precursor thin film formed in this step is a molybdenum amide thin film, or a thin film formed by the decomposition and/or reaction of a part of the molybdenum amide compound, and has a different composition from that of the intended molybdenum oxide thin film. The temperature at which this step is conducted is preferably room temperature to 500° C., more preferably 100 to 300° C.

Next, the unreacted molybdenum amide compound gas and by-produced gas are discharged from the deposition reaction unit (a step of discharging gases). Although it is ideal that the unreacted molybdenum amide compound gas and by-produced gas are completely discharged from the deposition reaction unit, they do not have to be completely discharged. Examples of the method for discharging gases may include a method involving purging the inside of the system with inert gas such as helium and argon, a method for discharging gases by reducing the pressure in the system, a method involving these methods in combination, and the like. The degree of pressure reduction in the case when the pressure is reduced is preferably 0.01 to 300 Pa, more preferably 0.1 to 100 Pa.

Next, oxidizing gas is introduced into the deposition reaction unit, and a molybdenum oxide thin film is formed from the precursor thin film obtained in the previous step of forming the precursor thin film by the action of the oxidizing gas, or the oxidizing gas and heat (a step of forming a molybdenum oxide thin film). The temperature during the action of heat in this step is preferably room temperature to 500° C., more preferably 100 to 300° C. The molybdenum amide compound according to the present invention has fine reactivity with oxidizing gas, and thus a molybdenum oxide thin film can be obtained.

Setting the deposition of the thin film by a series of operations consisting of the steps of introducing the starting material, the step of forming the precursor thin film, the step of discharging gases, and the step of forming the molybdenum oxide thin film mentioned above as one cycle, the cycle may be repeated plural times until a thin film having a necessary film thickness is obtained. In this case, it is preferable to conduct one cycle, then conduct the above-mentioned step of discharging gases in a similar manner to thereby discharge the unreacted molybdenum amide compound gas and oxidizing gas, and by-produced gas from the deposition reaction unit, and conduct the next one cycle.

Furthermore, in the formation of the molybdenum oxide thin film by the ALD process, energies such as plasma, light and voltage may be applied. The time for applying these energies is not specifically limited, and may be, for example, the time when the molybdenum amide compound gas is introduced in the step of introducing the starting material, the time of warming in the step of forming the molybdenum oxide thin film or the step of forming the molybdenum oxide thin film, the time when the gases in the system are discharged in the step of discharging gases, or the time when the oxidizing gas is introduced in the step of forming the molybdenum oxide thin film, or may be between the above-mentioned respective steps.

In the method for the manufacture of the thin film of the present invention, an annealing treatment may be conducted under an inert atmosphere, an oxidizing gas or a reductive gas atmosphere after the deposition of the thin film so as to obtain a better film quality, and in the case when embedding of steps is necessary, a reflow step may be provided. The temperature in such case is 400 to 1,200° C., specifically preferably 500 to 800° C.

Figure 2:
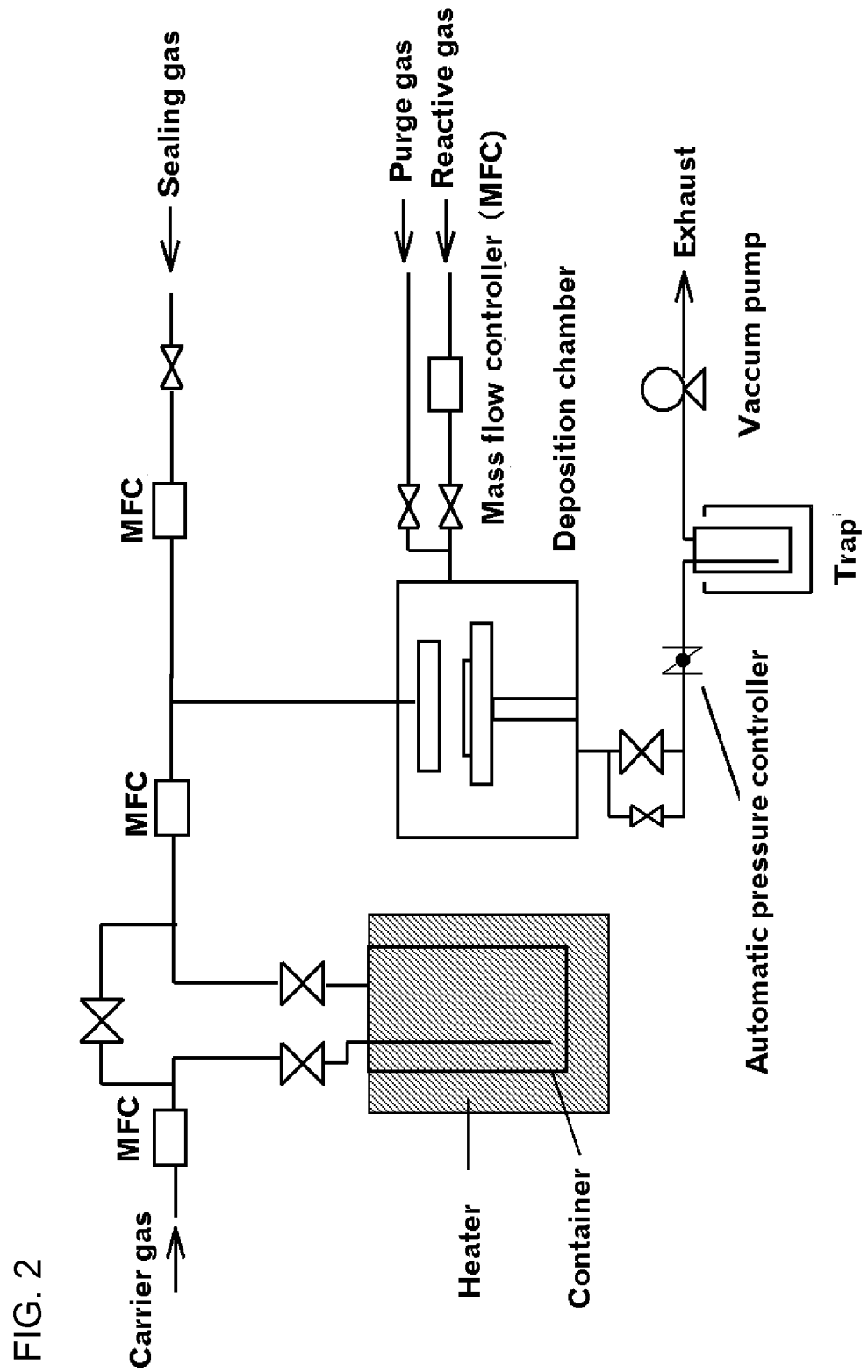
FIG. 2 is a schematic drawing showing another example of an apparatus for chemical vapor deposition, which is used for the method for manufacturing a molybdenum oxide-containing thin film of the present invention.
Figure 3:
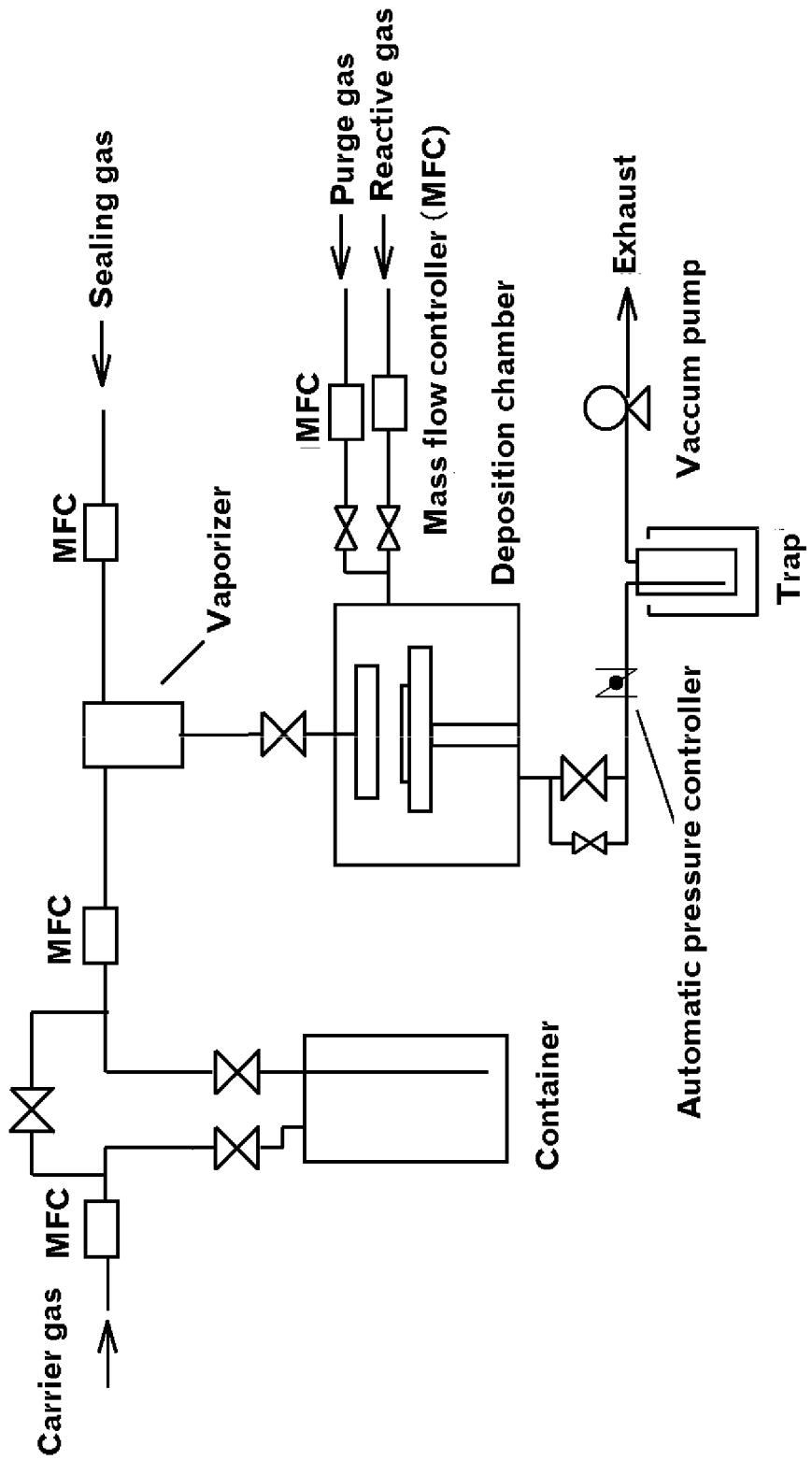
FIG. 3 is a schematic drawing showing still another example of an apparatus for chemical vapor deposition, which is used for the method for manufacturing a molybdenum oxide-containing thin film of the present invention.

As the apparatus used for the method for forming the thin film of the present invention, a well-known apparatus for a chemical vapor deposition process can be used. Specific examples of the apparatus may include a non-shower head type apparatus as shown in FIG. 1, an apparatus that can conduct a precursor by supplying bubbling as shown in FIG. 2, and an apparatus having a vaporizing chamber as shown in FIG. 3. Furthermore, not only the single wafer apparatuses as shown in FIG. 1, FIG. 2 and FIG. 3, but an apparatus using a batch furnace, which can treat plural wafers at the same time, can also be used.

Examples of the molybdenum oxide-containing thin film formed and manufactured by using the starting material for chemical vapor deposition of the present invention may include molybdenum dioxide, molybdenum trioxide, molybdenum-sodium-based composite oxides, molybdenum-calcium-based composite oxides, molybdenum-bismuth-based composite oxides, molybdenum-niobium-based composite oxides, molybdenum-zinc-based composite oxides, molybdenum-silicon-based composite oxides and molybdenum-cerium-based composite oxides, and examples of the purposes of use of these may include electronic parts and elements such as electrodes and barrier films, catalysts, starting materials for catalysts, starting materials for metals, metal surface-treating agents, additives for ceramics, additives for sintered metals, flame retarders, smoke suppressants, starting materials for antifreeze liquids, color developers for inorganic pigments, dye mordants for basic dyes, starting materials for anticorrosives, trace-element fertilizers for agriculture, and sub-starting materials for ceramic engineering.

The molybdenum amide compound according to the present invention is not specifically limited by the manufacture method therefor, and is manufactured by applying a well-known reaction. As the manufacture method, a well-known general synthesis method using a corresponding amide compound may be applied. Examples may include a method involving obtaining a reactive intermediate by a method for reacting a sodium acid salt of molybdenum, an amine and trimethylchlorosilane in 1,2-dimethoxyethane, and reacting the reactive intermediate with a dialkylamine.

Examples of the above-mentioned reactive intermediate may include an imide compound of molybdenum represented by the following general formula (III).

[Chemical Formula 12]

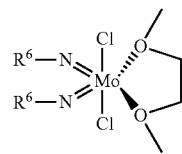

(III)

wherein $R^6$ represents a t-butyl group or t-amyl group.

In the synthesis example of the above-mentioned molybdenum amide compound, the molybdenum amide compound of the present invention represented by the following general formula (II), which can be obtained by reacting a reactive medium wherein $R^6$ is a t-amyl group among the compounds represented by the above-mentioned general formula (III) with a dialkylamine, is useful as a starting material for a chemical vapor deposition process, since the compound does not have halogen atoms such as fluorine in the structure and is a liquid having a high vapor pressure or a low melting point compound that becomes a liquid by slight warming, the device is not eroded by the reaction by-product in the manufacture of the molybdenum oxide-containing thin film by a chemical vapor deposition process, and the vaporizing property and the precursor-carrying performance are excellent.

[Chemical Formula 13]

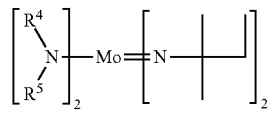

(II)

wherein $R^4$ and $R^5$ each represents a straight or branched alkyl group having 1 to 4 carbon atom(s).

EXAMPLES

The present invention will be further described in detail with reference to the following examples, evaluation examples and comparative examples. However, the present invention is in no way limited to the following examples and the like.

Manufacture Example 1

Manufacture of Compound No. 37

Under a dry argon gas atmosphere, 0.12 mol of sodium molybdate, 2.52 mol of 1,2-dimethoxyethane, 0.252 mol of t-amylamine, 0.48 mol of triethylamine and 0.96 mol of trimethylchlorosilane were charged in a 500 mL reaction flask, the temperature in the system was controlled to 80 to 82° C., and stirring was conducted for 12 hours. The solid content was filtered off by a 0.2 µm filter from the reaction solution, and the reaction solution was concentrated by removing the solvent by distillation under a reduced pressure to give a dark green slurry-like reactive intermediate at a yield of 95%. Subsequently, 0.114 mol of the reactive intermediate and 1.12 mol of dehydrated toluene were added to a reaction flask and dissolved, the solution was cooled to −20° C. by dry ice-isopropanol, 0.48 mol of dimethylamine gas was blown into the solution, and 140 mL of a 1.6 mol/L hexane solution of n-butyl lithium was added dropwise thereto and reacted. The reaction solution was gradually returned to room temperature and subsequently reacted by stirring for 2 hours. The solid substance was filtered off from the reaction solution by a 0.2 µm filter, the reaction solution was concentrated by distilling off the solvent under a reduced pressure, and the fraction at 195 Pa and a column top temperature of 103 to 104° C. was further separated from the reaction solution by distillation under a reduced pressure to give the intended product, compound No. 37. The collection rate by this purification was 60%. For the obtained yellowish orange liquid, the following analyses were conducted.

(Analytical Values)
(1) Elemental analysis (metal analysis: ICP-AES, chlorine analysis: TOX)
Molybdenum; 26.89 mass % (theoretical value 27.07%), Na; lower than 1 ppm, Cl; lower than 5 ppm
(2) $^1$H-NMR (solvent: deuterated benzene) (chemical shift: multiplicity:number of H)
(1.06:t:3) (1.35:s:6) (1.62:q:2) (3.46:s:6)
(3) TG-DTA
(Ar 100 ml/min, temperature rise 10° C./min, sample amount 8.836 mg) Temperature at 50 mass % loss 190° C.

Manufacture Example 2

Manufacture of Compound No. 38

Under a dry argon gas atmosphere, 0.12 mol of sodium molybdate, 2.52 mol of 1,2-dimethoxyethane, 0.252 mol of t-amylamine, 0.48 mol of triethylamine and 0.96 mol of trimethylchlorosilane were charged in a 500 mL reaction flask, the temperature in the system was controlled to 80 to 82° C., and stirring was conducted for 12 hours. The solid content was filtered off by a 0.2 µm filter from the reaction solution, and the reaction solution was concentrated by removing the solvent by distillation under a reduced pressure to give a dark green slurry-like reactive intermediate at a yield of 95%. Subsequently, 0.114 mol of the reactive intermediate and 1.12 mol of dehydrated toluene were added to a reaction flask and dissolved, the solution was cooled to −20° C. by dry ice-isopropanol, 0.48 mol of dimethylamine gas was blown into the solution, and 140 mL of a 1.6 mol/L hexane solution of n-butyl lithium was added dropwise thereto and reacted. The reaction solution was gradually returned to room temperature and subsequently reacted by stirring for 2 hours. The solid substance was filtered off from the reaction solution by a 0.2 μm filter, the reaction solution was concentrated by distilling off the solvent under a reduced pressure, and the fraction at 40 Pa and a column top temperature of 98 to 101° C. was further separated from the reaction solution by distillation under a reduced pressure to give the intended product, compound No. 38. The collection rate by this purification was 60%. For the obtained yellowish orange liquid, the following analyses were conducted.
(Analytical Values)
(1) Elemental analysis (metal analysis: ICP-AES, chlorine analysis: TOX)
Molybdenum; 25.31 mass % (theoretical value 25.09%), Na; lower than 1 ppm, Cl; lower than 5 ppm
(2) $^1$H-NMR (solvent: deuterated benzene) (chemical shift: multiplicity:number of H)
(1.02:t:2) (1.30:s:9) (1.59:q:3) (3.47:s:3) (3.67:q:2)
(3) TG-DTA
(Ar 100 ml/min, temperature rise 10° C./min, sample amount 12.009 mg)
Temperature at 50 mass % loss 209° C.

Evaluation Examples 1 to 7 and Comparative Examples 1-1 and 1-2

Evaluation of Physical Properties of Molybdenum Compounds

For the novel compounds Nos. 37 and 38 obtained by the above-mentioned Manufacture Examples, compounds Nos. 1, 2, 9, 73 and 74, which are known compounds, and comparative compounds 1 and 2 shown below, the state of each compound at an ordinary temperature under an ordinary pressure was visually observed, and for the solid compounds, the melting point was measured by using a micro melting point measuring apparatus, and the boiling point of each compound was measured. The results are shown in Table 1.
Comparative Compound 1
$MoF_6$
Comparative Compound 2
$Mo(CO)_6$

TABLE 1

| | Compound | State | Melting point | Boiling point |
| --- | --- | --- | --- | --- |
| Comparative Example 1-1 | Comparative Compound 1 | Liquid | 17° C. | 37° C. |
| Comparative Example 1-2 | Comparative Compound 2 | Solid | 150° C. | 156° C. |
| Evaluation Example 1 | Compound No. 1 | Liquid | — | 62° C./53 Pa |
| Evaluation Example 2 | Compound No. 2 | Liquid | — | 76° C./57 Pa |
| Evaluation Example 3 | Compound No. 9 | Liquid | — | 86° C./61 Pa |
| Evaluation Example 4 | Compound No. 37 | Liquid | — | 104° C./195 Pa |
| Evaluation Example 5 | Compound No. 38 | Liquid | — | 99° C./40 Pa |

TABLE 1-continued

| | Compound | State | Melting point | Boiling point |
| --- | --- | --- | --- | --- |
| Evaluation Example 6 | Compound No. 73 | Solid | ~50° C.*[1] | 40-70° C./1 Pa |
| Evaluation Example 7 | Compound No. 74 | Liquid | — | 65-90° C./0.1 Pa |

*[1]Although a clear melting point was not able to be measured, the compound was a solid at 25° C. and was a liquid at 50° C.

It was able to be confirmed from the above-mentioned Table 1 that Comparative Example 1-2 was a solid, whereas Evaluation Examples 1 to 7 were low melting point compounds, which are liquids or become liquids by slight warming. Furthermore, it was able to be confirmed that Comparative Examples 1-1 and 1-2, and Evaluation Examples 1 to 5 had low boiling points. Although comparative compounds 1 and 2 has low boiling points, comparative compound 1 has a small difference between the melting point and boiling point and thus is difficult to stably supply a starting material in a liquid state, and further has a problem that the compound erodes a device during film formation due to generation of hydrogen fluoride as a reaction byproduct, and comparative compound 2 has a smaller difference between the melting point and boiling point than that of comparative compound 1 and thus is difficult to stably supply a starting material in a liquid state stable; therefore, these compounds are not suitable as starting materials for chemical vapor deposition. It was able to be confirmed that the molybdenum amide compound according to the present invention is suitable as a starting material for chemical vapor deposition in that the compound does not contain halogen atoms such as a fluorine atom in the structure, and that the compound has a significant temperature difference between the melting point and boiling point and thus can stably retain its liquid state.

Evaluation Examples 8 to 11

Evaluation of Ozone Reactivity of Molybdenum Amide Compound

For comparative compound 2, compound No. 2, and compounds Nos. 37 and 38, a TG-DTA measurement was conducted under an ozone atmosphere. The measurement was conducted under conditions of oxygen with addition of 4% of ozone of 2,000 ml/min and temperature rise of 10° C./min. The presence or absence of the reactivity between the molybdenum compound and ozone was confirmed by the presence or absence of an exothermic peak accompanying with weight loss generated by the oxidative decomposition of the molybdenum compound by the ozone, and the residual amount at 300° C., at which the reaction is considered to have been sufficiently completed, was confirmed. The amounts of the samples were 3.275 mg to 8.447 mg. The results are shown in Table 2.

TABLE 2

| | Compound | Ozone reactivity (Reaction temperature) | Residual amount at 300° C. (cal.*[1]) |
| --- | --- | --- | --- |
| Evaluation Example 8 | Comparative compound 2 | ◯ (115° C.) | 30.6% (45.5%) |
| Evaluation Example 9 | Compound No. 2 | ◯ (130° C.) | 50.4% (59.3%) |
| Evaluation Example 10 | Compound No. 37 | ◯ (145° C.) | 50.5% (59.3%) |

TABLE 2-continued

| | Compound | Ozone reactivity (Reaction temperature) | Residual amount at 300° C. (cal.*[1]) |
|---|---|---|---|
| Evaluation Example 11 | Compound No. 38 | ○ (100° C.) | 50.3% (60.9%) |

*A calculated value of the residual amount when the residual component is considered as $MoO_3$.

From Table 2, it was found that, when the molybdenum amide compound according to the present invention has similar ozone reactivity to that of comparative compound 2, and the residual amount at 300° C. and the calculated value of the residual component in the case when the residual component is considered as $MoO_3$ were compared, the molybdenum amide compound according to the present invention had a smaller difference from the calculated value than that of comparative compound 2. Therefore, it was able to be confirmed that the molybdenum amide compound according to the present invention is converted to molybdenum oxide at a better yield ratio than that of comparative compound 2, and thus the molybdenum amide compound according to the present invention is useful as a starting material for producing a molybdenum oxide-containing thin film by a chemical vapor deposition process.

Example 1

Manufacture of Molybdenum Oxide Thin Film by ALD Process

Using compound No. 2 as a starting material for chemical vapor deposition, a molybdenum oxide thin film was manufactured on a silicon wafer by using the apparatus shown in FIG. 1 by an ALD process under the following conditions and involving the following steps. For the obtained thin film, the film thickness was measured by fluorescent X-ray, the composition ratio was analyzed by an X-ray photoelectron spectroscopy, and the composition was analyzed by X-ray diffraction were conducted. The results are shown in Table 3.

(Conditions)
Reaction temperature (substrate temperature); 240° C., reactive gas; ozone gas (Steps)
A series of steps consisting of the following (1) to (4) was set as one cycle, 50 cycles were repeated.
(1) Vapor of a starting material for chemical vapor deposition formed by vaporizing under conditions of a vaporizing chamber temperature of 70° C. and a vaporizing chamber pressure of 70 Pa is introduced and deposited under a system pressure of 100 Pa for 20 seconds.
(2) The unreacted starting material is removed by purging with argon for 15 seconds.
(3) Reactive gas is introduced, and a reaction is conducted under a system pressure of 80 Pa for 20 seconds.
(4) The unreacted starting material is removed by purging with argon for 15 seconds.

TABLE 3

| | Number of cycles | Film thickness | Composition ratio (Mo:O) | Composition |
|---|---|---|---|---|
| Example 1 | 50 times | 2.1 nm | 1.0:2.4 | $MoO_3$ |

It was found from the results in the above-mentioned Example 1 that, by using the molybdenum amide compound according to the present invention as a starting material for chemical vapor deposition, the compound is excellent in precursor carrying property and supplying property since the compound is a low melting point compound that is a liquid at an ordinary temperature under an ordinary pressure or becomes a liquid by slight warming, and thus a molybdenum oxide thin film having a fine film quality can be manufactured at high producibility.

The invention claimed is:

1. A method for manufacturing a molybdenum oxide-containing thin film, comprising, performing an Atomic Layer Deposition (ALD) process comprising
vaporizing a starting material for forming a thin film, the material comprising the compound No. 38:

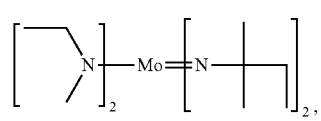

Compound No. 38 to obtain a vapor containing a molybdenum amide compound,
introducing the obtained vapor onto a substrate, and
further introducing ozone as an oxidizing gas at a temperature of between 100° C. to 300° C. to cause a decomposition and/or a chemical reaction to form a thin film on the substrate.

2. The method according to claim 1, wherein the starting material further comprises one or more organic coordinated compound(s) selected from the group consisting of alcohol compounds, glycol compounds, β-diketone compounds, cyclopentadiene compounds and organic amine compounds, with silicon or metals.

3. The method according to claim 2, wherein the metal is selected from the group consisting of lithium, sodium, potassium, magnesium, calcium, strontium, barium, titanium, zirconium, hafnium, vanadium, niobium, tantalum, molybdenum, manganese, iron, ruthenium, cobalt, rhodium, iridium, nickel, palladium, platinum, copper, silver, gold, zinc, aluminum, gallium, indium, germanium, tin, lead, antimony, bismuth, yttrium, lantern, cerium, praseodymium, neodymium, promethium, samarium, europium, gadolinium, terbium, dysprosium, holmium, erbium, thulium and ytterbium.

4. The method according to claim 1, wherein the oxidizing gas comprises at least one selected from the group consisting of oxygen, singlet oxygen, ozone, carbon dioxide, nitrogen monoxide, nitrogen dioxide, water, hydrogen peroxide, formic acid, acetic acid, and acetic anhydride.

5. The method according to claim 1, wherein the molybdenum oxide-containing thin film formed on the substrate comprise at least one selected from the group consisting of molybdenum dioxide, molybdenum trioxide, molybdenum-sodium-based composite oxides, molybdenum-calcium-based composite oxides, molybdenum-bismuth-based composite oxides, molybdenum-niobium-based composite oxides, molybdenum-zinc-based composite oxides, molybdenum-silicon-based composite oxides and molybdenum-cerium-based composite oxides.

6. The method according to claim 1, wherein the substrate is a silicon wafer.

* * * * *